(12) United States Patent
Etheridge

(10) Patent No.: US 11,474,090 B1
(45) Date of Patent: Oct. 18, 2022

(54) MOBILE SYSTEMS FOR MONITORING EMISSIONS

(71) Applicant: ENCINO ENVIRONMENTAL SERVICES, LLC, Alleyton, TX (US)

(72) Inventor: Joe Etheridge, Alleyton, TX (US)

(73) Assignee: ENCINO ENVIRONMENTAL SERVICES, LLC, Alleyton, TX (US)

( * ) Notice: Subject to any disclaimer, the term of this patent is extended or adjusted under 35 U.S.C. 154(b) by 0 days.

(21) Appl. No.: 17/485,762

(22) Filed: Sep. 27, 2021

(51) Int. Cl.
  *G01N 33/00* (2006.01)
  *G01N 21/25* (2006.01)
  *G01J 3/28* (2006.01)
  *G01N 21/17* (2006.01)

(52) U.S. Cl.
  CPC ........ *G01N 33/0036* (2013.01); *G01J 3/2823* (2013.01); *G01N 21/255* (2013.01); *G01J 2003/2826* (2013.01); *G01N 2021/1793* (2013.01)

(58) Field of Classification Search
  CPC . G01N 33/0036; G01N 33/004; G01J 3/2823; G01J 2003/2826
  See application file for complete search history.

(56) References Cited

U.S. PATENT DOCUMENTS

| | | | | |
|---|---|---|---|---|
| 7,149,366 B1 * | 12/2006 | Sun | ...................... | G01J 3/2823 382/284 |
| 8,013,303 B2 | 9/2011 | Erskov et al. | | |
| 9,719,879 B1 | 8/2017 | Tan et al. | | |
| 10,197,470 B2 | 2/2019 | Waxman et al. | | |

OTHER PUBLICATIONS

R. E. Arvidson, "FIDO prototype Mars rover field trials, Black Rock Summit, Nevada" (Year: 2002).*
NASA, "ChemCam" https://mars.nasa.gov/msl/spacecraft/instruments/chemcam/, Mar. 12, 2020 (Year: 2020).*
Jeffrey S. Norris, "PTEP: The Parallel Telemetry Processor", 2001 (Year: 2001).*
Maxime Bombrun, "Algorithm for particle detection and parameterization in high-frame-rate thermal video", Sep. 29, 2014 (Year: 2014).*
Xavier Watremez, "Remote Sensing Technologies for Detecting, Visualizing and Quantifying Gas Leaks" Apr. 2018 (Year: 2018).*
Wilburt, "Video Surveillance Platform" https://www.willburt.com/products/integrated-trailers/video-surveillance-platform/, Jun. 6, 2017 (Year: 2017).*
Wuxi Gallo Tech, https://www.made-in-china.com/showroom/wxgallo/product-detailqvdEwFalfLkn/China-Truck-Mounted-Telescoping-Mast-Broadcast-Vehicle-Telescopin . . . , Feb. 22, 2017 (Year: 2017).*

(Continued)

*Primary Examiner* — Maurice C Smith
(74) *Attorney, Agent, or Firm* — Hunton AK, LLP

(57) ABSTRACT

The present disclosure refers to a system for monitoring emissions. The system comprises an appliance with a mobile emission monitoring platform configured to identify and quantify a gas emission; an optional rangefinder configured to determine a size of a gas emission plume and a velocity of the gas emission plume; and an imaging device configured to provide an image. The appliance is mounted to an extendable mast on, for example, a trailer such that the system may provide mobile and continuous monitoring of emissions.

19 Claims, 2 Drawing Sheets

(56) References Cited

OTHER PUBLICATIONS

Standard Trailer Hitch Mount—Manual https://www.larsonelectronics.com/product/145898/40-foot-telescoping-light-mast-13-40-four-stage-tower-standard-trailer-hitch-mount-manual Jul. 2, 2021 (Year: 2021).*

Ricardo Gardener, "X-Dragon Solar Charger Review (40W Solar Panel Charger)", https://www.youtube.com/watch?v=OgZtOrzdJ7c, 2020 (Year: 2020).*

Opli, "Telops Launches the Hyper-Cam Methane, a Unique Imaging Sensor which Detects, Identifies and Quantifies Atmospheric Methane Concentrations", https://www.opli.net/opli_magazine (Year: 2016).*

A2Z "A2Z WM & AWM series Mechanical Manual Winch Telescopic MastSystems" Jan. 20, 2020 (Year: 2020).*

Libia Gonzalez, "Development Of A Low-Cost Network Of Webcams For Monitoring Plant Phenology In A Chihuahuan Desert Shrubland", 2011 (Year: 2011).*

Yang, Zhi-xiong, "The principle and state research on gas identification method for longwave infrared hyperspectral imaging", Applied Optics, 2019 (Year: 2019).*

Airborne Laser Methane Assessment, Leaders in Gas Detection Alma System, pp. 1-2, Control Equipment Pty Ltd, ABN 23 009 838 582.

Kim-Hak, David et al, Fugitive Methane Emission Identification and Source Attribution: Ethane-to-Methan Analysis using a Portable Cavity, p. 1, Picarro.

Emission Measuring Campaigns, p. 1-2.

Laser absorption spectroscopy: A new perspective in emission monitoring, pp. 1-8, International Labmate Limited, Jul. 27, 2020.

Tan, Dongjie et al., Research on Airborne Infrared Leakage Detection of Natural Gas Pipeline, Proc. of SPIE, vol. 8006, pp. 1-7, 2011.

Laser-Based System Offers Continuous Monitoring of Leaks from Oil and Gas Operations, pp. 1-4, Mar. 22, 2018, OSA The Optical Society.

Methane leak Detection Technologies Technical Workshop, pp. 1-196, Sep. 2018, National Association of Regulatory Utility Commissioners.

\* cited by examiner

MOBILE SYSTEMS FOR MONITORING EMISSIONS

FIELD OF THE DISCLOSURE

The present disclosure relates to a mobile system for monitoring emissions such as, for example, methane.

BACKGROUND AND SUMMARY

Traditional emissions monitoring systems are stationary, complex apparatuses that either intermittently or continuously monitor emissions of gases from, for example, refineries, chemical plants, power plants, or other sources of gaseous emissions. Unfortunately, such traditional systems are immobile and therefore incapable of being moved to, for example, monitor a different location that may be more in need of monitoring. Moreover, such traditional systems are often capable of or configured to only detect one type of emission. In addition, traditional emissions monitoring systems were incapable of processing any data on-site. Thus, use of traditional systems often required transmitting or transporting acquired data to another location for processing and analyzing as to whether remedial action or intervention was required at the source of emission.

What is needed are more effective and cost-efficient systems for monitoring emissions. It would further be advantageous if such systems were mobile, capable of monitoring more than one type of emission, and/or could process data on-site. Advantageously, the system described herein may meet one or more up to all of the aforementioned needs.

The present application generally pertains to a system for monitoring emissions. The system may comprise a mobile emission monitoring platform configured to identify and quantify a gas emission. The system may also comprise a rangefinder configured to determine a size of a gas emission plume and a velocity of the gas emission plume and an imaging device configured to provide an image. One or more up to all of the emission monitoring platform, the optional rangefinder, and the imaging device may be operably connected to a processor. The emission monitoring platform, the optional rangefinder, and the imaging device may be mounted to an extendable mast which may be mounted to a trailer.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Various embodiments of the present disclosure, together with further objects and advantages, may best be understood by reference to the following description taken in conjunction with the accompanying drawings.

DETAILED DESCRIPTION

Figure 1:
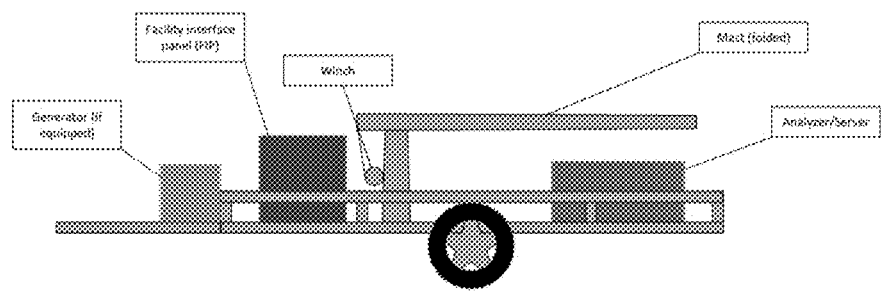
FIG. 1 shows a trailer with a folded mast and other components of a system for monitoring emissions.

The following description of embodiments provides a non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

The systems for monitoring emissions typically comprise a mobile emission monitoring platform configured to identify and quantify a gas emission; an optional rangefinder configured to determine a size of a gas emission plume and a velocity of the gas emission plume; and an imaging device configured to provide an image. In this manner the system may be configured to continuously monitor a facility emitting an emission.

Mobile Emission Monitoring Platform

The type of mobile emission monitoring platform is not particularly critical so long as it is capable of identifying and/or quantifying a volume or amount of gas emission of a specific gas or gases to be monitored. Such gases to be monitored by the systems described herein may include, for example, a hydrocarbon such as a C1-C6 hydrocarbon like methane or propane, carbon dioxide ($CO_2$), volatile organic compounds (VOCs), hydrogen sulfide ($H_2S$), and the like. In some embodiments the mobile emission monitoring platform may comprise a camera that may scan visible, ultraviolet, and/or near-infrared spectral ranges. Such cameras include, for example, hyperspectral cameras configured to identify and/or quantify a volume or amount of gas emission of a specific gas or gases to be monitored. Such cameras may capture a gas or mixture of gases unique infrared absorption to assist in identifying and quantifying an emission. In some embodiments a hyperspectral camera may be configured to identify and quantify two or more up to seven or more different gases. Similarly, in some embodiments the system may be configured to identify and quantify a gas emission wherein said gas emission comprises two or more gases or even a mixture of three or more gases.

The emission monitoring platform may be powered by any convenient source. In some embodiments the same power source may power the emission monitoring platform and other components of the system. Such power supplies may include, for example, uninterruptible power supplies. Suitable power supplies include, for example, facility power, a generator, a solar array, etc. The emission monitoring platform and/or other components described herein may in some embodiments be operably connected to a processor.

Rangefinder

If desired, a rangefinder may also be included in the systems of the present application. Suitable rangefinders may vary depending upon the other components, the emission, and the desired capability or specificity. Typically, a suitable rangefinder is one configured to determine a size of a gas emission plume and a velocity of the gas emission plume. In some embodiments the rangefinder may facilitate a more accurate measurement of the size of the emission based on its proximity to the camera. As described above for the mobile emission monitoring platform any suitable power source may be employed and the rangefinder may also be operably connected to a processor.

Imaging Device

An imaging device may also be included in the systems of the present application. Suitable imaging devices may vary depending upon what type of image is desired, e.g., photo, video, and/or combination thereof. The imaging device may also be powered by any suitable power source which source may be the same or different than that for the mobile emission monitoring platform and/or rangefinder. As with the other components described above, the imaging device may be operably connected to a processor.

Other Components

The system may include other components which may vary depending upon the desired characteristics of the system. Such components include, for example, a facility interface panel. A facility interface panel may be configured to power and/or control the system. Components such as a photoionic or other cameras or sensor may be employed. A processor may also be employed and operably connected to the emission monitoring platform, the rangefinder, the imaging device, and/or a facility interface panel.

The processor may assist in processing data from the various components and may be configured to provide a user with various data points, provide notices of certain conditions, and/or provide signals about corrective actions in regard to an emission. For example, the processor may be configured to provide a notice upon a gas emission above a threshold level or provide a user with an actual emission rate. Additionally or alternatively, a processor may be configured to provide a user with an actual emission rate per activity, an actual emission rate per a piece of equipment, or any combination thereof. In some embodiments the processor may be configured to provide a user with a summary image of an emissions event. Such a summary image may comprise, for example, a hyperspectral image of emission concentration on a visual image of a field of view. A processor may be configured to provide a user with a recorded video of an emissions event. Such a recorded video may comprise an emission concentration a visual image of a field of view. The processor may be configured to provide data such as one or more up to all of the following: hyperspectral data, system telemetry, emission data comprising an emission source, an emission volume, an emission frequency, and/or any combination thereof.

Extendable Mast

In some embodiments the emission monitoring platform, the rangefinder, and/or the imaging device and other components are each mounted to an extendable mast. In its extended position in a substantially vertical direction an extendable mast may allow for each component to have a more unobstructed aerial view or line of sight of an emission source. Each of the aforementioned components may be mounted to a separate extendable mast but in most embodiments it may be suitable to mount the components to the same extendable mast. In some embodiments at least two up to all of the emission monitoring platform, the rangefinder, and the imaging device are housed within an appliance which appliance is mounted to the extendable mast. Such an appliance protects the individual components from damage due to wind, rain, snow, etc. and in addition substantially aligns the line of sight of the individual components to the emission source or sources of interest. Furthermore, housing the individual components in the appliance facilitates the mounting to the extendable mast.

The extendable mast may be configured to be mounted to a vehicle or a trailer for mobility. Such vehicles are not particularly limited and may be a car, truck, semitrailer, boat, or other convenient vehicle depending upon the desired operation. The height of the extendable mast and the location of the appliance on the extendable mast may vary depending upon, for example, the distance and location of the emission source or sources to be monitored. In some embodiments the location of the appliance on the extendable mast be moved up or down via a convenient means such as a winch or an actuator (hydraulic or mechanical). In some embodiments the system is configured such that emissions may be observed from a lateral distance of from about 25 meters up to about 150 meters. In some embodiments the extendable mast may be a telescoping mast that extends up to about 40 feet or more in a substantially vertical direction relative to the ground.

FIG. 1 shows a trailer with a folded mast and other components of a system for monitoring emissions. A generator on the trailer may supply power to a facility interface panel that controls the system. A folded mast which may or may not be telescoping may be extended with a winch or other suitable mechanism to a desired height for monitoring emissions. A processor and/or server may analyze and process data locally and be configured to transmit signals to an operator and/or to the emission source being monitored. The appliance with the emission monitoring platform, the rangefinder, and/or the imaging device may be conveniently stored for security when not in operation.

Figure 2:
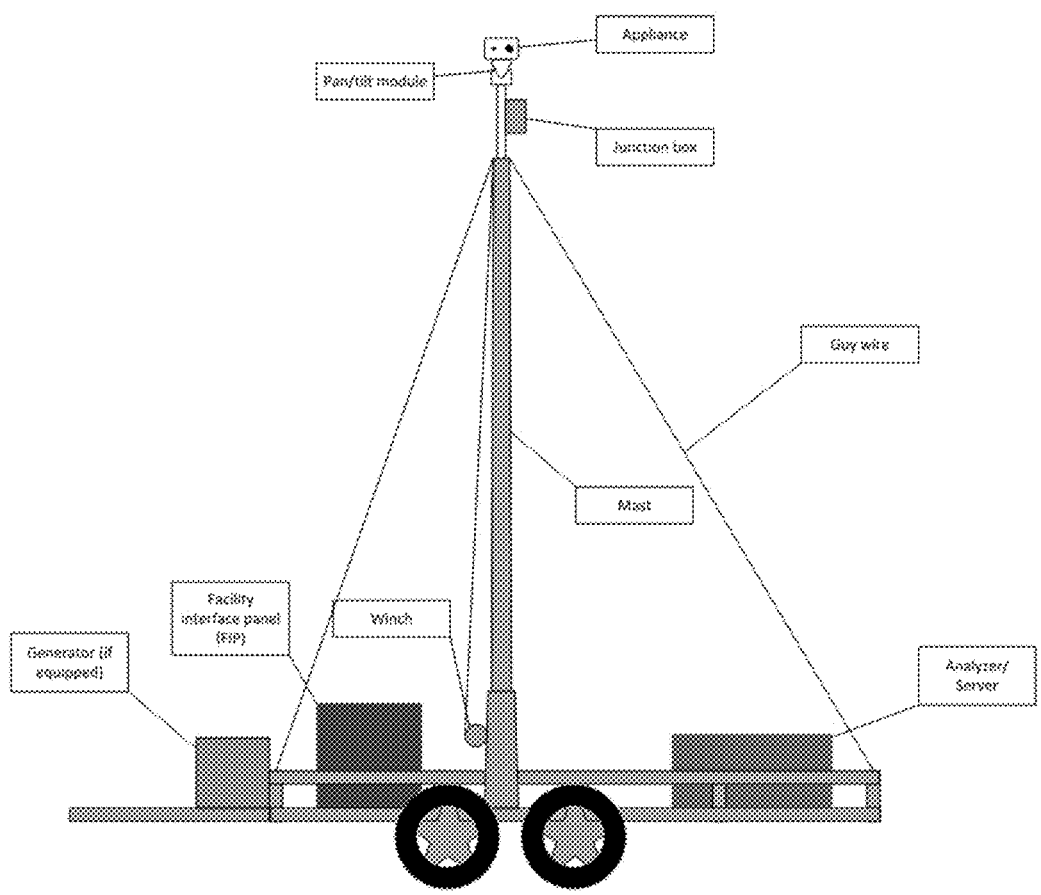
FIG. 2 shows a trailer with an extended mast and other components of a system for monitoring emissions.
Figure 3:
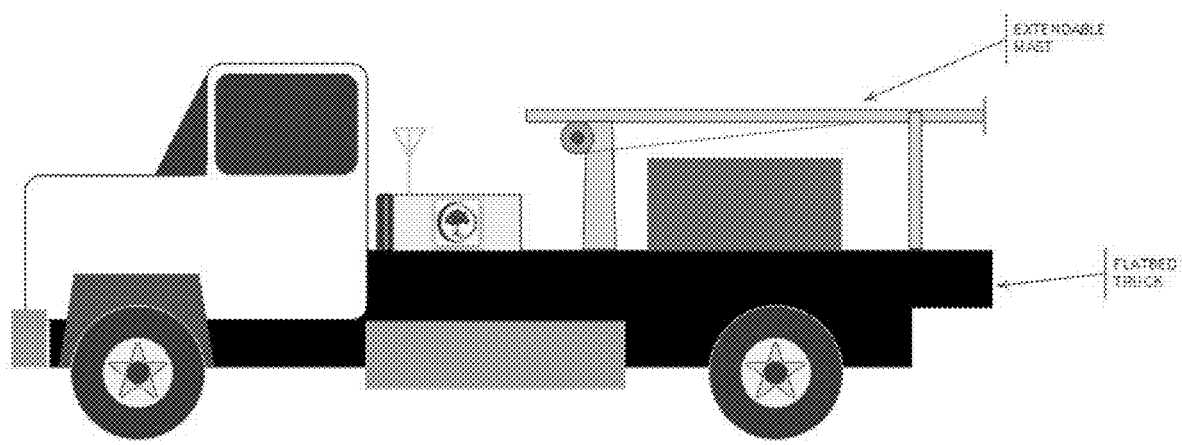
FIG. 3 shows a truck with a folded extendable mast and other components of a system for monitoring emissions.
Figure 4:
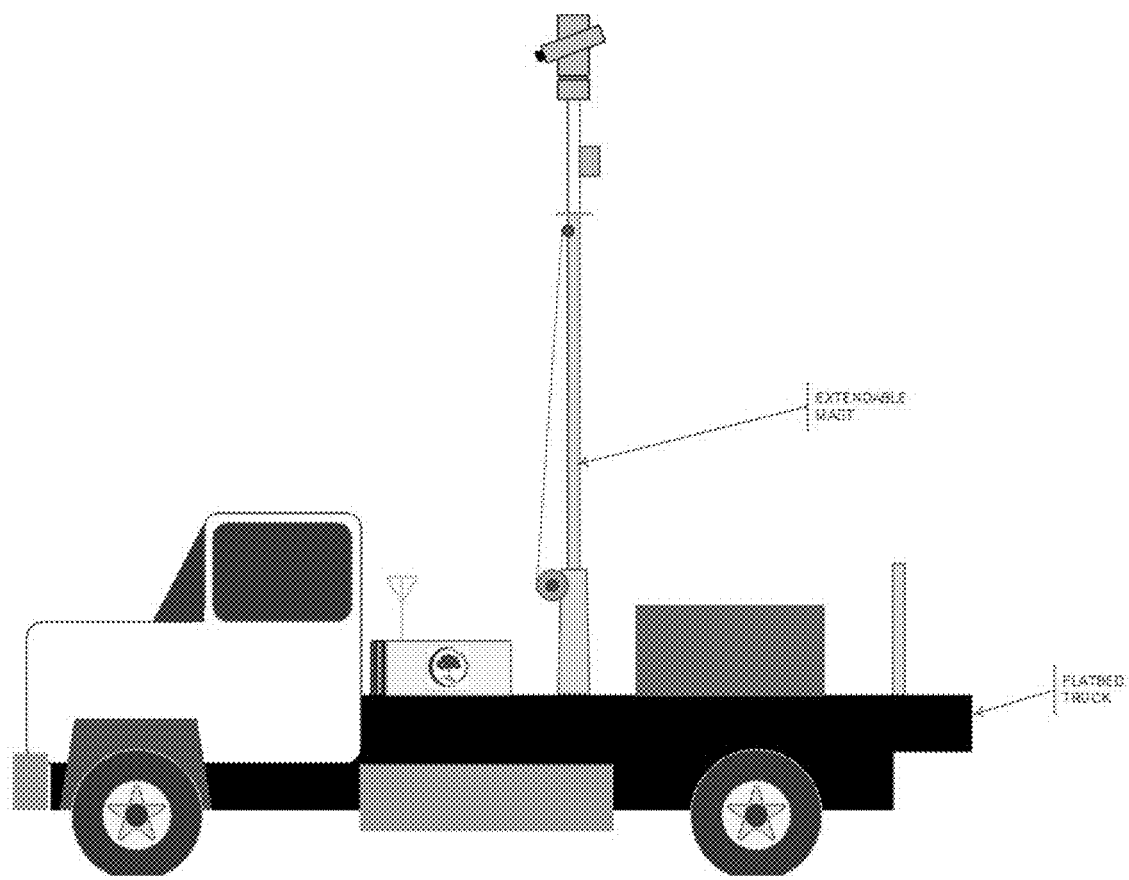
FIG. 4 shows a truck with an extended mast and other components of a system for monitoring emissions.

FIG. 2 shows the trailer with the attached appliance in an extended position. A remotely operated pan/tilt module provides for precise positioning of the appliance for emission monitoring.

In the preceding specification, various embodiments have been described with references to the accompanying drawings. It will, however, be evident that various modifications and changes may be made thereto, and additional embodiments may be implemented, without departing from the broader scope of the invention as set forth in the claims that follow. The specification and drawings are accordingly to be regarded as an illustrative rather than restrictive sense.

I claim:

1. A system for monitoring emissions comprising:
   a mobile emission monitoring platform configured to identify and quantify a gas emission wherein the gas emission comprises a C1-C6 hydrocarbon, volatile organic compound, hydrogen sulfide, carbon dioxide, or a mixture thereof;
   and
   an imaging device configured to provide an image;
   wherein the emission monitoring platform and the imaging device are each operably connected to a processor; and
   wherein the emission monitoring platform and the imaging device are each mounted to an extendable mast and wherein the extendable mast is configured to be mounted to a car, a truck, or a trailer;
   wherein the system further comprises a facility interface panel configured to power and control the system and wherein the system further comprises at least one guy wire to support the extendable mast.

2. The system of claim 1 further comprising a rangefinder configured to determine a size of a gas emission plume and a velocity of the gas emission plume.

3. The system of claim 2 further comprising an appliance mounted to the extendable mast and wherein the appliance houses at least two or more of the emission monitoring platform, the rangefinder, and the imaging device.

4. The system of claim 1 wherein the gas emission comprises methane and the emission monitoring platform comprises a hyperspectral imaging device.

5. The system of claim 1 wherein the facility interface panel is configured to be powered by facility power, a generator, a solar array, or any combination thereof.

6. The system of claim 1 wherein the processor is configured to provide a notice upon a gas emission above a threshold level.

7. The system of claim 1 wherein the processor is configured to provide a user with an actual emission rate.

8. The system of claim 1 wherein the processor is configured to provide a user with an actual emission rate per activity, an actual emission rate per a piece of equipment, or any combination thereof.

9. The system of claim 1 wherein the processor is configured to provide a user with a summary image of an emissions event wherein said summary image comprises a hyperspectral image of emission concentration on a visual image of a field of view.

10. The system of claim 1 wherein the processor is configured to provide a user with a recorded video of an emissions event wherein said recorded video comprises an emission concentration.

11. The system of claim 1 wherein the processor is configured to provide a user with hyperspectral data and system telemetry.

12. The system of claim 1 wherein the processor is configured to provide a user with emission data comprising an emission source, an emission volume, an emission frequency, or any combination thereof.

13. The system of claim 3 wherein the appliance is configured to allow for 360 degree monitoring of a facility emitting an emission.

14. The system of claim 3 wherein the appliance is configured to observe emissions at from about 25 meters up to about 150 meters.

15. The system of claim 1 wherein the system is configured to continuously monitor a facility emitting an emission.

16. The system of claim 1 wherein the extendable mast is mounted on a trailer and wherein the extendable mast is configured to extend substantially vertical relative to the ground.

17. The system of claim 1 wherein the extendable mast is a telescoping mast that extends up to about 40 feet in a substantially vertical direction relative to the ground.

18. The system of claim 1 wherein the emission monitoring platform is configured to identify and quantify a gas emission wherein said gas emission comprises two or more gases.

19. The system of claim 1 wherein the system further comprises a winch for moving the extendable mast up or down.

* * * * *